United States Patent
Amano et al.

(10) Patent No.: US 8,251,892 B2
(45) Date of Patent: Aug. 28, 2012

(54) ACTION DISPLAY SYSTEM AND ENDOSCOPE SYSTEM

(75) Inventors: Shoichi Amano, Hachioji (JP); Seigo Ito, Hachioji (JP); Atsushi Ogawa, Hachioji (JP); Masanobu Koitabashi, Hachioji (JP); Takashi Sawai, Hachioji (JP); Harutaka Adachi, Ome (JP)

(73) Assignee: Olympus Medical Systems Corp. (JP)

( * ) Notice: Subject to any disclaimer, the term of this patent is extended or adjusted under 35 U.S.C. 154(b) by 959 days.

(21) Appl. No.: 12/269,356

(22) Filed: Nov. 12, 2008

(65) Prior Publication Data

US 2009/0131750 A1 May 21, 2009

(30) Foreign Application Priority Data

Nov. 15, 2007 (JP) .................................. 2007-296993

(51) Int. Cl.
*A61B 1/04* (2006.01)
(52) U.S. Cl. ....................................................... 600/109
(58) Field of Classification Search .................. 600/109, 600/111, 145
See application file for complete search history.

(56) References Cited

U.S. PATENT DOCUMENTS

| 5,060,632 A | 10/1991 | Hibino et al. ...................... 128/6 |
| 2007/0173694 A1* | 7/2007 | Tsuji et al. ..................... 600/146 |
| 2009/0131750 A1* | 5/2009 | Amano et al. ................. 600/109 |
| 2011/0270036 A1* | 11/2011 | Kawai et al. .................. 600/118 |
| 2011/0275892 A1* | 11/2011 | Tanaka .......................... 600/109 |

FOREIGN PATENT DOCUMENTS

JP 8-180825 7/1996

OTHER PUBLICATIONS

Extended Search Report by the European Patent Office for European Patent Application No. 08019838.5-23019 issued Feb. 26, 2009.

* cited by examiner

*Primary Examiner* — W. B. Perkey
(74) *Attorney, Agent, or Firm* — Ostrolenk Faber LLP

(57) ABSTRACT

An action display system includes an action instruction signal generating portion configured to generate an action instruction signal for instructing an action of an acting portion in response to an input to an input portion, an action control portion configured to control a drive portion such that the acting portion acts in accordance with the action instruction signal, the action control portion switchable between a regular mode to enable an action of the acting portion with the first and second degrees of freedom and an action disabled mode to disable an action of the acting portion with one degree of freedom, an image obtaining portion configured to obtain an image associated with an action state of the acting portion, and a display portion configured to display an index associated with the regular mode and the action disabled mode of the action control portion together with the image.

7 Claims, 6 Drawing Sheets

US 8,251,892 B2

ACTION DISPLAY SYSTEM AND ENDOSCOPE SYSTEM

CROSS-REFERENCE TO RELATED APPLICATIONS

This application is based upon and claims the benefit of priority from prior Japanese Patent Application No. 2007-296993, filed Nov. 15, 2007, the entire contents of which are incorporated herein by reference.

BACKGROUND OF THE INVENTION

1. Field of the Invention

The present invention relates to an action display system wherein an acting portion is configured to act with two degrees of freedom and the acting portion is configured to be operated based on an input to an input portion while observing an image associated with an action state of the acting portion, e.g., an endoscope system wherein a bending portion is configured to act to bend with two degrees of freedom and the bending portion is configured to be operated based on an input to an input portion while observing an observation image associated with a bending action state of the bending portion.

2. Description of the Related Art

There are used various action display systems wherein an acting portion is configured to act with two degrees of freedom and the acting portion is configured to be operated based on an input to an input portion while observing an image associated with an action state of the acting portion.

In Jpn. Pat. Appln. KOKAI Publication No. 8-180825 discloses a scanning electron microscope as an action display system. In this scanning electron microscope, a sample support on which a sample is mounted is arranged on an XY stage configured to move in X and Y directions. A control table is connected with the XY stage through a control system. A track ball configured to operate the XY stage is arranged on the control table. Further, an observation image obtained by the scanning electron microscope is to be displayed on a CRT display. That is, the XY stage is configured to operated by means of the track ball while observing an observation image associated with a movement state of the XY stage. Furthermore, operating a switch portion of the control table enables restricting the movable direction of the XY stage to the X direction alone or the Y direction alone. Moreover, a light emitting element configured to indicate movable directions of the XY stage is arranged on the control table.

BRIEF SUMMARY OF THE INVENTION

In an aspect of the present invention, an action display system includes: an acting portion configured to act with first and second degrees of freedom; an input portion configured to accept an input for operating the acting portion; a drive portion configured to actuate the acting portion; an action instruction signal generating portion configured to generate an action instruction signal for instructing an action of the acting portion in response to an input to the input portion; an action control portion configured to control the drive portion such that the acting portion acts in accordance with the action instruction signal, the action control portion switchable between a regular mode to enable an action of the acting portion with the first and second degrees of freedom and an action disabled mode to disable an action of the acting portion with one degree of freedom; an image obtaining portion configured to obtain an image associated with an action state of the acting portion; and a display portion configured to display an index associated with the regular mode and the action disabled mode of the action control portion together with the image.

In another aspect of the present invention, an endoscope system includes: an endoscope including a bending portion configured to act to bend in first two directions forming a first degree of freedom and second two directions forming a second degree of freedom, the endoscope configured to obtain an observation image associated with a bending action state of the bending portion; an input portion configured to accept an input for actuating the bending portion to bend; a drive portion configured to actuate the bending portion to bend; an action instruction signal generating portion configured to generate an action instruction signal for instructing a bending action of the bending portion in response to an input to the input portion; an action control portion configured to control the drive portion such that the bending portion acts to bend in accordance with the action instruction signal, the action control portion switchable between a regular mode to enable a bending action of the bending portion with the first and second degrees of freedom and an action disabled mode to disable a bending action of the bending portion with one degree of freedom; a display portion configured to display an index associated with the regular mode and the action disabled mode of the action control portion together with the image.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Each embodiment according to the present invention will now be explained with reference to the drawings hereinafter.

FIGS. 1 to 7C show a first embodiment of the present invention.

Figure 1:
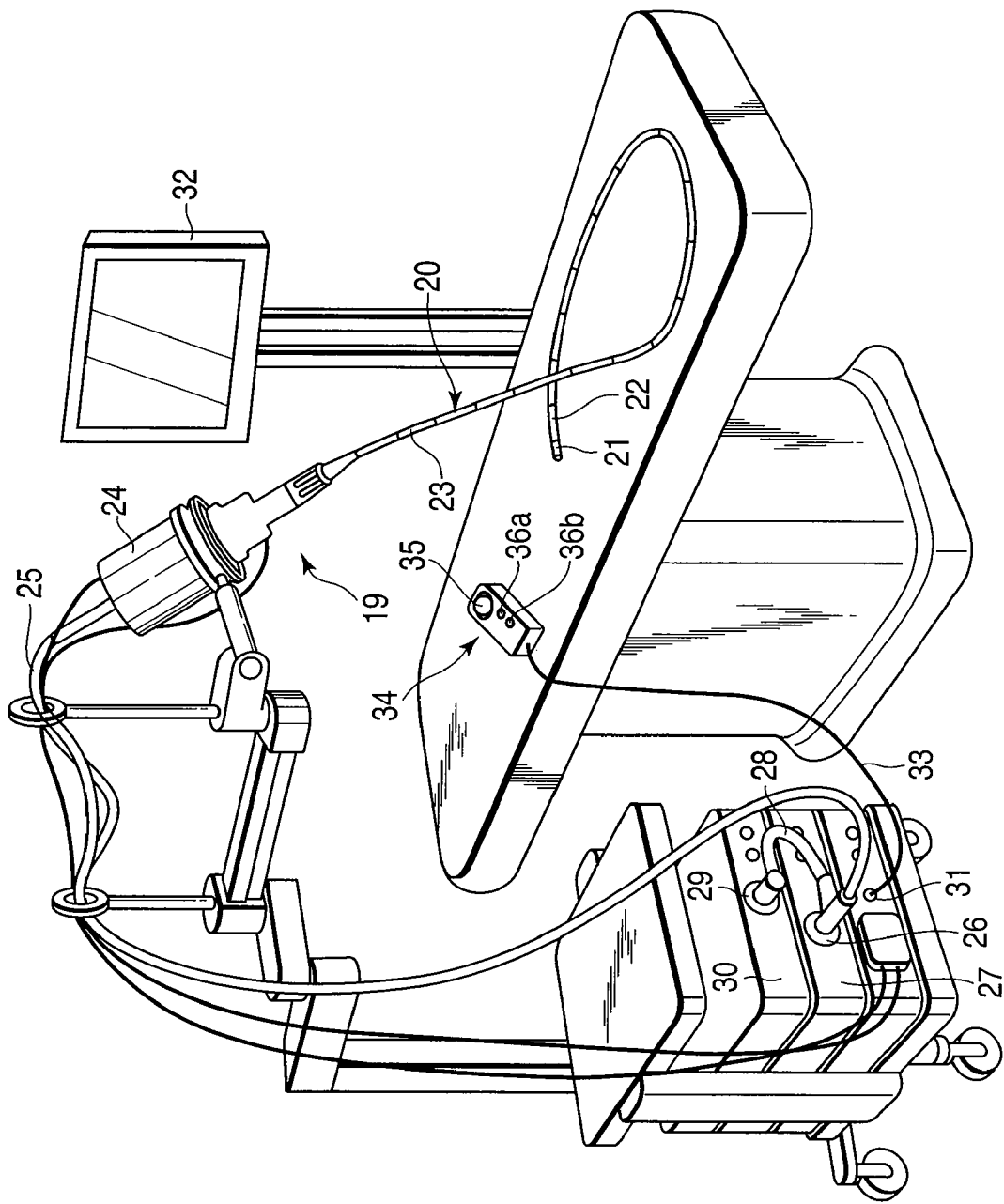
FIG. 1 is a perspective view showing an endoscope system according to a first embodiment of the present invention.

An outline structure of an endoscope system as an operation system will now be explained with reference to FIG. 1. The endoscope system includes an endoscope 19 as an image obtaining portion. The endoscope 19 includes an elongated insertion portion 20 configured to be inserted into the interior of the body. In the insertion portion 20, a distal-end rigid portion 21, a bending portion 22, and an insertion tube portion 23 are sequentially provided from a distal end side to a proximal end side. The distal-end rigid portion 21 includes a built-in illumination optical system configured to illuminate an observation target and a built-in image pick-up unit configured to pick up an image thereof. The bending portion 22 as an acting portion can act to bend up/down and left/right, forming first and second degrees of freedom, with respect to an observation view field of the endoscope 19. The insertion tube portion 23 is long and flexible. A proximal end portion of the insertion portion 20 is detachably connected with a drive unit 24. Angle wires configured to bend the bending portion 22 are inserted through the insertion portion 20 from the bending portion 22 to the proximal end portion of the insertion portion 20. When the angle wires are pulled and loosened by means of the drive unit 24, the bending portion 22 acts to bend. A universal cord 25 is extended from the drive unit 24, and a light source connector 26 at an extended end portion of the universal cord 25 is connected with a light source device 27. Illumination light generated by the light source device 27 is supplied to an illumination optical system at a distal end portion of the endoscope 19 through a light guide inserted through the endoscope 19. An electric cord 28 is extended from the light source connector 26, and an electric connector 29 at an extended end portion of the electric cord 28 is connected with a video processor 30. An image signal obtained in the image pick-up unit at the distal end of the endoscope 19 is output to the video processor 30 through signal lines inserted through the endoscope 19. A monitor 32 as a display portion configured to display various images is connected with the video processor 30. Further, a system controller 31 is connected with the video processor 30. An operation portion 34 configured to operate the endoscope system is connected with the system controller 31 through an operation cord 33.

Figure 2:
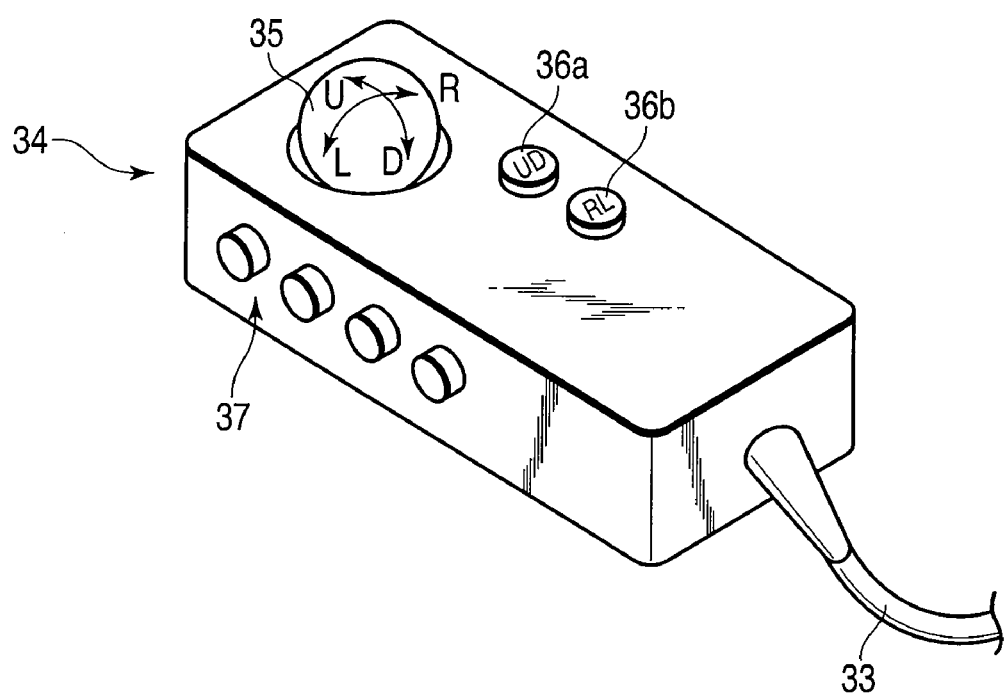
FIG. 2 is a perspective view showing an operation portion according to the first embodiment of the present invention.

A structure of the operation portion 34 will now be explained with reference to FIG. 2. A track ball 35 is arranged in the operation portion 34 and an input to actuate the bending portion 22 to bend can be performed by means of the track ball 35 as an input portion. The track ball 35 can rotate in arbitrary directions. Here, respective rotational directions of the track ball 35 for actuating the bending portion 22 to bend up/down alone or left/right alone are orthogonal to each other as indicated by arrows in FIG. 2, and these respective rotational directions will be referred to as an up/down direction and a left/right direction of the track ball 35. Furthermore, a UD disable switch 36a and an LR disable switch 36b configured to respectively disable up/down and left/right bending actions of the bending portion 22 are arranged in the operation portion 34. Moreover, various kinds of switches 37 configured to operate, e.g., an image pick-up action of the endoscope 19 are arranged in the operation portion 34.

Bending action control in the endoscope system will now be explained with reference to FIGS. 3 to 5.

Figure 3:
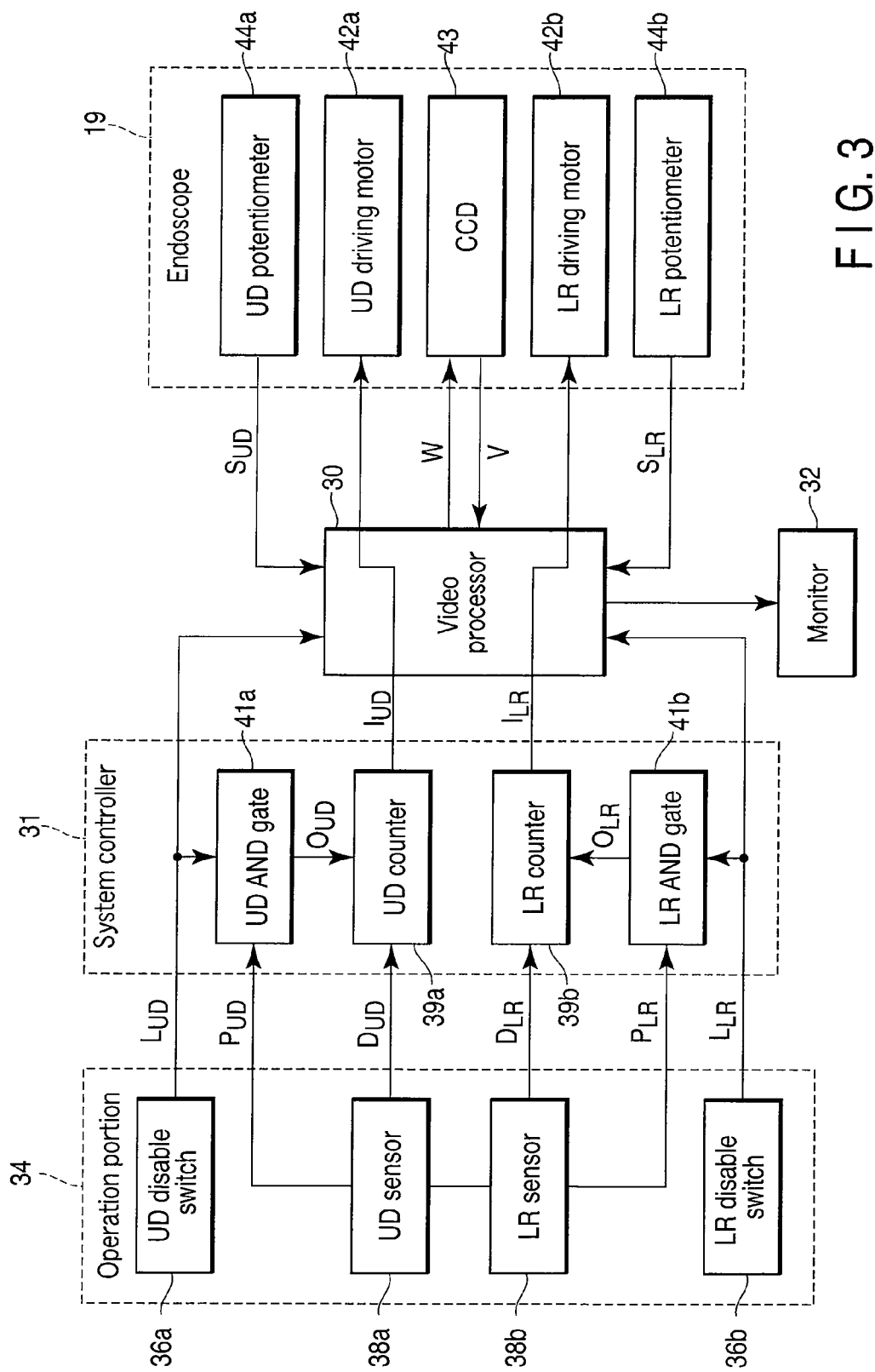
FIG. 3 is a block diagram showing the endoscope system according to the first embodiment of the present invention.

Referring to FIG. 3, the operation portion 34 includes a built-in UD sensor 38a configured to detect a rotational direction and rotational amount of the track ball 35 regarding up/down directions. The UD sensor 38a forming an action instruction signal generating portion generates an up/down bending direction instruction signal $D_{UD}$ as an action instruction signal corresponding to the rotational direction and an up/down bending amount instruction signal $P_{UD}$ as an action instruction signal corresponding to the rotational amount. The up/down bending direction instruction signal $D_{UD}$ becomes binary one when the rotational direction is upward, and binary zero when the same is downward. The up/down bending amount instruction signal $P_{UD}$ is a pulse signal including a pulse number corresponding with a rotational amount. As the UD sensor 38a, a non-contact optical sensor is used, for example.

On the other hand, a UD disable switch 36a is arranged in the operation portion 34. The UD disable switch 36a is configured to generate an up/down bending disable signal $L_{UD}$. The up/down bending disable signal $L_{UD}$ becomes binary one when the UD disable switch 36a is off, and it becomes binary zero when the same is on.

The up/down bending direction instruction signal $D_{UD}$ generated by the UD sensor 38a is to be output to a UD counter 39a of the system controller 31. Moreover, the up/down bending amount instruction signal $P_{UD}$ generated by the UD sensor 38a and the up/down bending disable signal $L_{UD}$ generated by the UD disable switch 36a are to be output to a UD AND gate 41a of the system controller 31. A UD AND gate output signal $O_{UD}$ generated by the UD AND gate becomes the same pulse signal as the up/down bending amount instruction signal $P_{UD}$ when the UD disable switch 36a is off and the up/down bending disable signal $L_{UD}$ is binary one, and it becomes binary zero when the UD disable switch 36a is on and the up/down bending disable signal $L_{UD}$ is binary zero. The UD AND gate output signal $O_{UD}$ is to be output to a UD counter 39a. The UD counter 39a generates an up/down bending order signal $I_{UD}$ based on the up/down bending instruction signal $D_{UD}$ and the UD AND gate output signal $O_{UD}$. The up/down bending order signal $I_{UD}$ is to actuate the bending portion 22 to bend up when the up/down bending instruction signal $D_{UD}$ is binary one and down when the same is binary zero with a bending amount proportional to a pulse number of the UD AND gate output signal $O_{UD}$. Therefore, the up/down bending order signal $I_{UD}$ is to actuate the bending portion 22 to bend with a bending amount proportional to the pulse number of the up/down bending amount instruction signal $P_{UD}$ when the UD disable switch 36a is off and is not to actuate the bending portion 22 to bend up/down, irrespective of the up/down bending amount instruction signal $P_{UD}$ when the UD disable switch 36a is on.

The up/down bending order signal $I_{UD}$ generated by the UD counter 39a is to be output to a UD driving motor 42a forming a drive portion of the drive unit 24 of the endoscope 19 through the video processor 30. The UD driving motor 42a is configured to drive a UD sprocket in the drive unit 24 to rotate based on the up/down bending order signal $I_{UD}$ to pull and loosen one end side and the other end side of a UD angle wire wound around the UD sprocket, and to actuate the bending portion 22 to bend up/down.

There are same in a case of the left/right direction. An LR sensor 38b, an LR disable switch 36b, an LR AND gate 41b, and an LR counter 39b forming an action instruction signal generating portion generate a left/right bending instruction signal $D_{LR}$, a left/right bending amount instruction signal $P_{LR}$, a left/right bending disable signal $L_{LR}$, an LR AND gate output signal $O_{LR}$, and a left/right bending order signal $I_{LR}$ as action instruction signals, respectively. An LR driving motor 42b forming a drive portion is configured to actuate the bending portion 22 to bend left/right through an LR sprocket and an LR angle wire.

In this manner, the UD AND gate 41a, the LR AND gate 41b, the UD counter 39a, and the LR counter 39b form an action control portion.

A case where the bending portion 22 is bent in one direction alone will now be explained in detail with reference to FIGS. 4 and 5.

Figure 4:
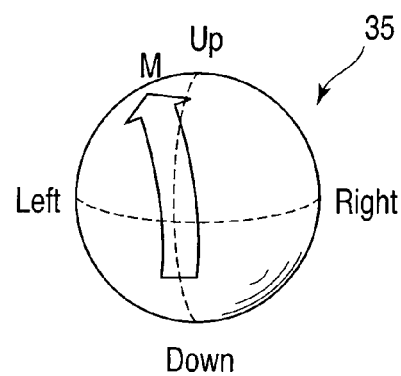
FIG. 4 is a schematic view showing a rotating operation of a track ball in one direction according to the first embodiment of the present invention.
Figure 5:
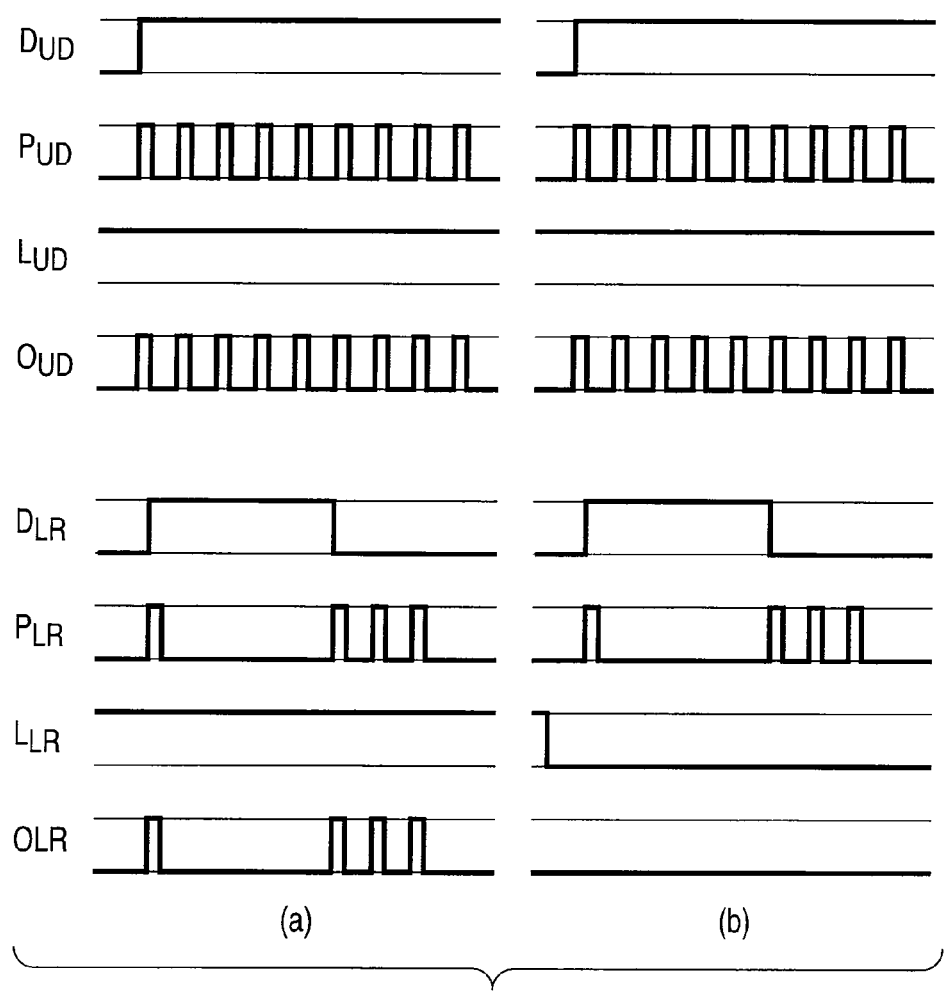
FIG. 5 is a timing chart showing bending control of the endoscope system according to the first embodiment of the present invention.

When attempting to rotate the track ball 35 in the upward direction alone as indicated by an arrow M in FIG. 4, left/right rotation occurs in addition to the desired upward rotation.

That is, as shown in FIGS. 5(a) and (b), in response to start of upward rotation of the track ball 35, the up/down bending instruction signal $D_{UP}$ changes from binary zero to binary one, and the up/down bending amount instruction signal $P_{UD}$ as a pulse signal including a pulse number corresponding with a rotational amount is generated. Since the UD disable switch 36a is off, the up/down bending disable signal $L_{UD}$ is binary one, and the UD AND gate output signal $O_{UD}$ becomes the same pulse signal as the up/down bending amount instruction signal $P_{UD}$.

On the other hand, based on left/right rotation of the track ball 35, the left/right bending instruction signal $D_{LR}$ changes from binary zero to binary one and then from binary one to binary zero, and the left/right bending amount instruction signal $P_{LR}$ as a pulse signal including a pulse number corresponding with a rotational amount is generated. As shown in FIG. 5(a), when the LR disable switch 36b is off, the left/right bending disable signal $L_{LR}$ is binary one, and the LR AND gate output signal $O_{LR}$ becomes the same pulse signal as the left/right bending amount instruction signal $P_{LR}$. Therefore, the left/right bending order signal $I_{LR}$ is to actuate the bending portion 22 to bend left/right. On the contrary, as shown in FIG. 5(b), when the LR disable switch 36b is on, the left/right bending disable signal $L_{LR}$ is binary zero, and the LR AND gate output signal $O_{LR}$ is binary zero. Therefore, the left/right bending instruction signal $I_{LR}$ is not to actuate the bending portion 22 to bend left/right.

Image control in the endoscope system will now be explained with reference to FIGS. 3 and 6 to 7A.

Referring to FIG. 3, a drive signal W is to be output from the video processor 30 to a CCD 43 in the image pick-up unit, and an image signal V obtained by the CCD 43 is to be output to the video processor 30. The video processor 30 is configured to process the image signal V and to generate an observation image. Further, a UD potentiometer 44a is configured to detect rotational amount of the UD sprocket corresponding with up/down bending amount of the bending portion 22, and the UD potentiometer 44a is configured to output a UD detection signal $S_{UD}$ to the video processor 30. In regard to the left/right direction, likewise, an LR potentiometer 44b is configured to output an LR detection signal $S_{LR}$ to the video processor 30. The video processor 30 is configured to process the UD detection signal $S_{UD}$ and the LR detection signal $S_{LR}$ and to generate a bending position image representing a bending position of the bending portion 22. Furthermore, the LR disable switch 36b and the UD disable switch 36a is configured to output the up/down bending disable signal $L_{UD}$ and the left/right bending disable signal $L_{LR}$ to the video processor 30. The video processor 30 is configured to process the up/down bending disable signal $L_{UD}$ and the left/right bending disable signal $L_{LR}$ and to generate a bending allowance image as an index indicative of a bendable direction of the bending portion 22. It is noted that although the video processor 30 is configured to generate the bending position image and the bending allowance image in the present invention, the system controller 31 may be configured to generate these images and the video processor 30 may be configured to perform a superimpose process of these images.

Figure 6:
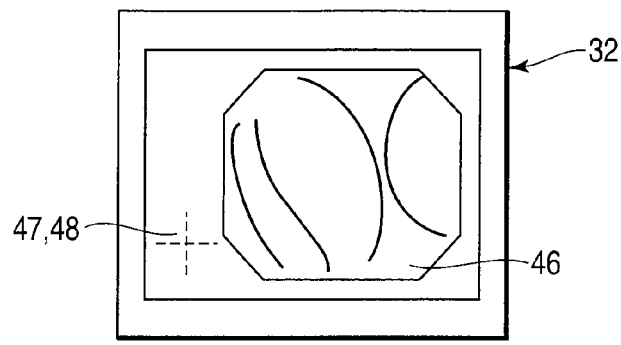
FIG. 6 is a schematic view showing a display image of a monitor according to the first embodiment of the present invention.

Referring to FIG. 6, a bending position image 47 and a bending allowance image 48 are superimposed and displayed on the same screen of the monitor 32, and an observation image 46, and the bending position image 47 and the bending allowance image 48 are displayed in proximity to each other.

The bending position image 47 will now be explained with reference to FIGS. 7A to 7C. In the bending position image 47, the ordinate represents a UD axis indicative of an up/down bending position, and the abscissa represents an LR axis indicative of a left/right bending position. Capital letters "U", "D", "L", and "R" standing for the up, down, left, and right directions are provided at both ends of each axis. A black point is arranged at a position corresponding to a bending position of the bending portion 22 with respect to the UD axis and the LR axis. Therefore, it is possible to recognize the bending position of the bending portion 22 from the position of the black point.

The bending allowance image 48 will now be explained with reference to FIGS. 7A to 7C.

Figure 7A:
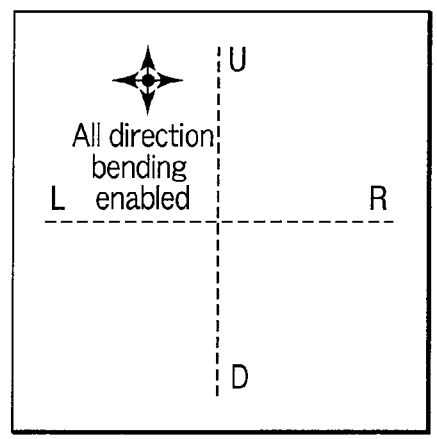
FIG. 7A is a schematic view showing a UDLR allowance image of a bending allowance image according to the first embodiment of the present invention.

As shown in FIG. 7A, when the bending portion 22 is not disabled from acting to bend and can act to bend up, down, left, and right, the bending allowance image 48 is a UDLR allowance image. That is, the UD axis, the capital letters "U" and "D", the LR axis, and the capital letters "L" and "R" are displayed. Furthermore, four arrows extending up, down, left, and right from the black point are displayed. It is possible to intuitively recognize from these images that the bending portion 22 can act to bend up, down, left, and right. Moreover, a message that "All direction bending enabled" is displayed near the black point.

Figure 7B:
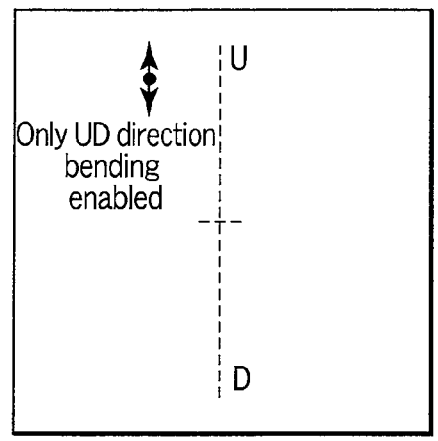
FIG. 7B is a schematic view showing a UD allowance image of the bending allowance image according to the first embodiment of the present invention.

As shown in FIG. 7B, when the bending portion 22 is disabled from acting to bend left/right and can only act to bend up/down, the bending allowance image 48 is a UD allowance image. That is, the UD axis and the capital letters "U" and "D" are displayed, but the LR axis and the capital letters "L" and "R" are erased. However, in order to show an original point position as the bending position image 47, the central part of the LR axis remains without being erased. Additionally, although the two arrows extending up/down from the black point are displayed, the two arrows extending left/right are erased. It is possible to intuitively recognize from these images that the bending portion 22 can only act to bend up/down. Further, a message "Only UD direction bending enabled" is displayed near the black point.

Figure 7C:
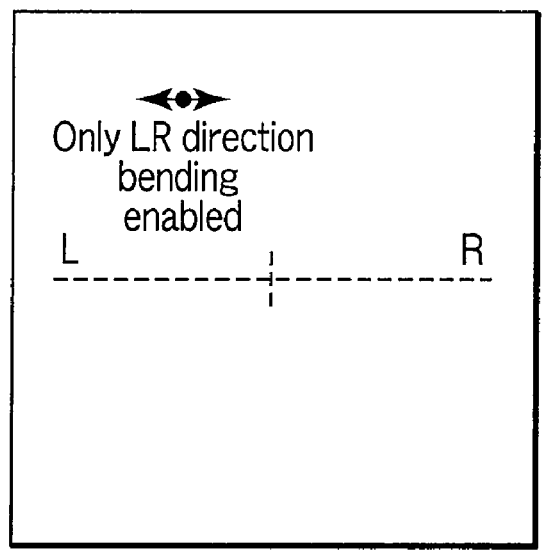
FIG. 7C is a schematic view showing an LR allowance image of the bending allowance image according to the first embodiment of the present invention.

As shown in FIG. 7C, when the bending portion 22 is disabled from acting to bend up/down and can only act to bend left/right, the bending allowance image 48 is an LR allowance image. That is, the LR axis and the capital letters "L" and "R" are displayed, but the UD axis and the capital letters "U" and "D" are erased. However, in order to show an original point position as the bending position image 47, the central part of the UD axis remains without being erased. Furthermore, the two arrows extending left/right from the black point are displayed, but the two arrows extending up/down are erased. It is possible to intuitively recognize from these images that the bending portion 22 can only act to bend left/right. Moreover, a message "Only LR bending enabled" is displayed near the black point.

A method of using the endoscope system according to this embodiment will now be explained.

The insertion portion 20 of the endoscope 19 is inserted into the interior of the body to observe the interior of the body. When desiring a movement of an observation position, the track ball 35 of the operation portion 34 is operated to rotate while observing the observation image 46, and so the bending portion 22 act to bend up, down, left, and right. Since the bending position image 47 is displayed near the observation image 46 on the screen of the monitor 32, a bending position of the bending portion 22 can be recognized while observing the observation image 46. Additionally, when desiring the bending portion 22 to bend up/down or left/right alone, especially when desiring a bending position to be adjusted finely, the LR disable switch 36b or the UD disable switch 36a is turned on to disable left/right or up/down bending so that the bending portion 22 cannot bend in a non-intended direction, and then the track ball 35 is operated to rotate. When the LR disable switch 36b or the UD disable switch 36a is turned on, the bending allowance image 48 becomes the UD allowance image or the LR allowance image, and the bending allowance image 48 is displayed near the observation image 46. Therefore, it is possible to recognize a bendable direction while observing the observation image 46 without transferring gaze to the operation portion 34 located at an operator's hand. Furthermore, even if the LR disable switch 36b or the UD disable switch 36a is erroneously operated to disable the bending operation in a non-intended direction, it is possible to detect the erroneous operation based on the bending allowance image 48. Therefore, it is prevented that an erroneous action of the bending portion 22 occurs due to a following operation of the track ball 35. The bending position of the bending portion 22 is adjusted, and then an observation and a treatment are performed in the interior of the body. When the observation and the treatment requires a relatively long time, a bendable direction of the bending portion 22 may be forgotten. However, since the bending allowance image 48 continues to be displayed, when again desiring a movement of the observation position, it is possible to recognize the bendable direction while observing the observation image 46. Furthermore, the bending allowance image 48 is displayed near the observation image 46 and keeping observation of the observation image 46 causes the bending allowance image 48 to get into an operator's eyes. Therefore, it is possible to prevent an erroneous action of the bending portion 22 by a following operation of the track ball 35 due to forgetting a disablement of a bending of the bending portion 22.

Thus, the endoscope system according to this embodiment demonstrates the following effect.

In the endoscope system according to this embodiment, the bending portion 22 is enabled to act to bent up/down or left/right alone as required, and the bending portion 22 is bent while observing the observation image 46 associated with a bending action of the bending portion 22. Here, since the observation image 46 and the bending allowance image 48 are displayed in proximity to each other in the same screen, it is possible to visually confirm the bending allowance image 48 to readily recognize which direction of up/down and left/right, up/down alone, and left/right alone the bending portion 22 can act to bend in and to operate the bending portion 22 rapidly and assuredly.

In the foregoing embodiment, the observation image 46, and the bending position image 47 and the bending allowance image 48 are displayed in proximity to each other, but they may be displayed such that the bending position image 47 and the bending allowance image 48 partially overlap on the observation image 46.

Figure 8:
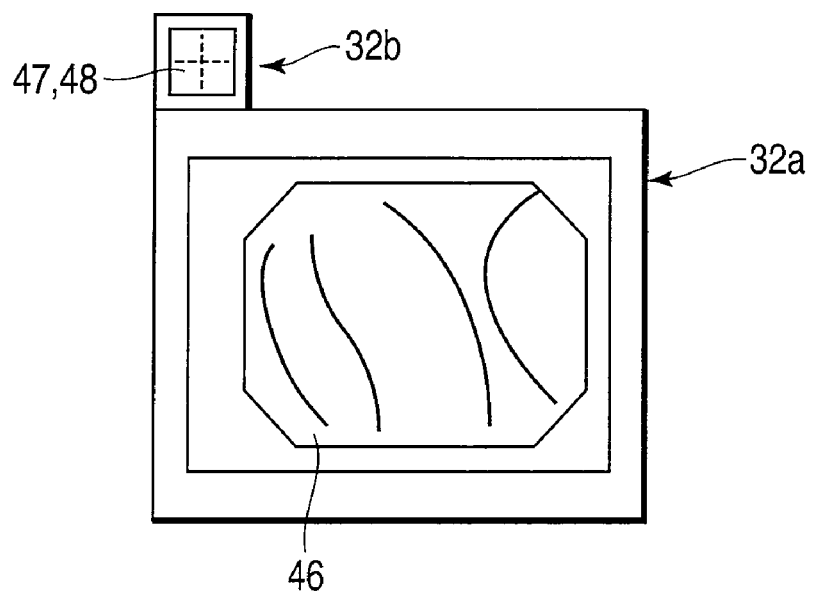
FIG. 8 is a schematic view showing first and second monitors according to a second embodiment of the present invention.

FIG. 8 shows a second embodiment of the present invention.

In an endoscope system according to this embodiment, as a display portion, a second monitor 32b configured to display a bending position image 47 and a bending allowance image 48 is used in addition to a first monitor 32a configured to display an observation image 46 of an endoscope 19. The second monitor 32b is sufficiently smaller than the first monitor 32a, portable, and can be arranged at a good position to be watched near the first monitor 32a. Since the observation image 46, and the bending position image 47 and the bending allowance image 48 are displayed on the different monitors 32a and 32b in this manner, a degree of freedom of display of the observation image 46 in a screen is increased as compared with a case where these images are displayed on the same monitor 32, and so it is possible to facilitate observation of the observation image 46, e.g., due to an enlarging display of the observation image 46.

In the foregoing embodiment, although a track ball is used as an input portion, any input portion configured to instruct an action with two degrees of freedom, e.g., a joystick or a mouse may be used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An action display system comprising:
    an acting portion configured to act with first and second degrees of freedom;
    an input portion configured to accept an input for operating the acting portion;
    a drive portion configured to actuate the acting portion;
    an action instruction signal generating portion configured to generate an action instruction signal for instructing an action of the acting portion in response to an input to the input portion;
    an action control portion configured to control the drive portion such that the acting portion acts in accordance with the action instruction signal, the action control portion switchable between a regular mode to enable an action of the acting portion with the first and second degrees of freedom and an action disabled mode to disable an action of the acting portion with one degree of freedom;
    an image obtaining portion configured to obtain an image associated with an action state of the acting portion; and
    a display portion configured to display an index associated with the regular mode and the action disabled mode of the action control portion together with the image.

2. The action display system according to claim 1, wherein the action disabled mode includes a first action disabled mode to disable an action of the acting portion with the first degree of freedom and a second action disabled mode to disable an action of the acting portion with the second degree of freedom, and
    the index includes an index associated with the regular mode, the first action disabled mode, and the second action disabled mode of the action control portion.

3. The action display system according to claim 1, wherein the index and the image are displayed in proximity to each other.

4. The action display system according to claim 1, wherein the display portion includes a monitor configured to display the index and the image on the same screen.

5. The action display system according to claim 1, wherein the display portion includes a first monitor configured to display the index and a second monitor configured to display the image.

6. An endoscope system comprising:
    an endoscope including a bending portion configured to act to bend in first two directions forming a first degree of freedom and second two directions forming a second degree of freedom, the endoscope configured to obtain an observation image associated with a bending action state of the bending portion;

an input portion configured to accept an input for actuating the bending portion to bend;

a drive portion configured to actuate the bending portion to bend;

an action instruction signal generating portion configured to generate an action instruction signal for instructing a bending action of the bending portion in response to an input to the input portion;

an action control portion configured to control the drive portion such that the bending portion acts to bend in accordance with the action instruction signal, the action control portion switchable between a regular mode to enable a bending action of the bending portion with the first and second degrees of freedom and an action disabled mode to disable a bending action of the bending portion with one degree of freedom;

a display portion configured to display an index associated with the regular mode and the action disabled mode of the action control portion together with the image.

7. The endoscope system according to claim 6, wherein the action disabled mode includes a first action disabled mode to disable a bending action of the bending portion in the first two directions and a second action disabled mode to disable a bending action of the bending portion in the second two directions, and the index includes an index associated with the regular mode, the first action disabled mode, and the second action disabled mode of the action control portion.

* * * * *